(12) United States Patent
Watson et al.

(10) Patent No.: US 10,463,315 B2
(45) Date of Patent: Nov. 5, 2019

(54) ADAPTIVE ALARM FOR PHYSIOLOGICAL MONITORING

(71) Applicant: COVIDIEN LP, Mansfield, MA (US)

(72) Inventors: James Nicholas Watson, Edinburgh (GB); Paul S. Addison, Edinburgh (GB); Graeme A. Lyon, Edinburgh (GB)

(73) Assignee: Covidien LP, Mansfield, MA (US)

( * ) Notice: Subject to any disclaimer, the term of this patent is extended or adjusted under 35 U.S.C. 154(b) by 882 days.

(21) Appl. No.: 14/947,688

(22) Filed: Nov. 20, 2015

(65) Prior Publication Data

US 2016/0155309 A1 Jun. 2, 2016

Related U.S. Application Data

(60) Provisional application No. 62/085,952, filed on Dec. 1, 2014.

(51) Int. Cl.
*A61B 5/1455* (2006.01)
*A61B 5/00* (2006.01)

(52) U.S. Cl.
CPC ........ *A61B 5/7282* (2013.01); *A61B 5/14552* (2013.01); *A61B 5/746* (2013.01)

(58) Field of Classification Search
USPC ....................................................... 600/310
See application file for complete search history.

(56) References Cited

U.S. PATENT DOCUMENTS

| | | | |
|---|---|---|---|
| 5,349,953 A | * | 9/1994 | McCarthy ............ A61B 5/1455 600/323 |
| 5,865,736 A | | 2/1999 | Baker, Jr. et al. |
| 6,754,516 B2 | | 6/2004 | Mannheimer |
| 7,123,950 B2 | | 10/2006 | Mannheimer |
| 7,215,984 B2 | | 5/2007 | Diab et al. |
| 7,215,986 B2 | | 5/2007 | Diab et al. |
| 7,254,433 B2 | | 8/2007 | Diab et al. |
| 7,328,053 B1 | | 2/2008 | Diab et al. |
| 7,376,453 B1 | | 5/2008 | Diab et al. |
| 7,383,070 B2 | | 6/2008 | Diab et al. |
| 8,401,606 B2 | | 3/2013 | Mannheimer |
| 8,622,919 B2 | | 1/2014 | Haartsen et al. |
| 2004/0215069 A1 | | 10/2004 | Mannheimer |
| 2007/0032714 A1 | | 2/2007 | Mannheimer |
| 2007/0208259 A1 | | 9/2007 | Mannheimer |
| 2007/0225575 A1 | | 9/2007 | Kilborn et al. |
| 2007/0225580 A1 | | 9/2007 | Wang |
| 2008/0183058 A1 | | 7/2008 | Mannheimer |

(Continued)

*Primary Examiner* — Eric F Winakur
*Assistant Examiner* — Marjan Fardanesh
(74) *Attorney, Agent, or Firm* — Shumaker & Sieffert, P.A.

(57) ABSTRACT

A technique for managing alarms includes acquiring a physiological parameter value and one or more alarm settings associated with the physiological parameter value. The technique also includes determining if the one or more alarm settings are associated with an adaptive alarm manager selecting an adaptive alarm condition from a plurality of adaptive alarm conditions when the one or more alarm settings are associated with the adaptive alarm manager; determining if the physiological parameter value meets the selected adaptive alarm condition; and generating an alarm in response when the physiological parameter value meets the selected adaptive alarm condition.

17 Claims, 3 Drawing Sheets

(56) References Cited

U.S. PATENT DOCUMENTS

| | | |
|---|---|---|
| 2008/0214906 A1 | 9/2008 | Wang et al. |
| 2011/0213212 A1* | 9/2011 | Al-Ali ................ A61B 5/14551 600/300 |
| 2012/0029301 A1* | 2/2012 | Battista, Jr. ............ A61B 5/746 600/300 |

* cited by examiner

ADAPTIVE ALARM FOR PHYSIOLOGICAL MONITORING

CROSS-REFERENCE TO RELATED APPLICATIONS

The present application claims the benefit of U.S. Provisional Application No. 62/085,952, which was filed on Dec. 1, 2014, and entitled "ADAPTIVE ALARM FOR PHYSIOLOGICAL MONITORING", the disclosure of which is incorporated herein by reference in its entirety.

BACKGROUND

The present disclosure relates generally to alarm management in medical devices, and in particular to a system and method for improving the clinical significance of alarms.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Alarm management in medical facilities is drawing attention as an important aspect of medical care. Alarms are generated by many types of medical devices, including monitoring devices (for example, capnography monitors, pulse oximeters, heart rate monitors, and others) and therapeutic devices (for example, ventilators, infusion pumps, and others). These medical devices generate alarms based on patient conditions, device status, and stored alarm algorithms. The purpose of these alarms is to alert caregivers when the patient's condition may be deteriorating, in case medical intervention is needed, or when the medical device may not be operating properly. The alarm system may result in a greater probability of detection and response to medical conditions that would benefit from awareness or action on the part of the caregiver.

Nuisance alarms—alarms that do not correspond to a clinically significant event—are of concern in many medical facilities. Nuisance alarms may be caused by false readings by the medical equipment, or by conservative or sub-optimal alarm algorithms that trigger when the patient's physiological condition has not changed in a significant way. Nuisance alarms resulting from false positive alarm conditions may reduce the overall effectiveness of an alarm system. Certain techniques may mitigate or reduce the occurrence of nuisance alarms. For example, rather than triggering alarms based on conventional alarm settings, which are dependent on the instantaneous excursions of a measured value outside a range, alarms may instead be delayed until a deviation has occurred that is either sufficiently large or sufficiently long relative to an alarm threshold value. In this manner, certain types of alarms, e.g., momentary small value changes that return quickly to normal, may be suppressed. However, certain clinicians may wish to have more granularity in alarm sensitivity while also reducing nuisance alarms.

SUMMARY

In a first embodiment, a method is provided that includes acquiring a physiological parameter value and a first alarm setting defining a first alarm condition. The method also includes generating a first alarm instruction upon a determination that the physiological parameter value meets the first alarm condition and identifying a sensitivity of the first alarm setting. The method also includes generating a second alarm instruction upon a determination that the physiological parameter meets a second alarm condition wherein the second alarm condition is selected based on the sensitivity of the first alarm setting and triggering an alarm in response to the first alarm instruction or the second alarm instruction.

In a second embodiment, a method is provided that includes acquiring a physiological parameter value and acquiring one or more alarm settings associated with the physiological parameter value. The method also includes, when the one or more alarm settings are associated with an adaptive alarm manager, selecting an adaptive alarm condition from a plurality of adaptive alarm conditions based on a sensitivity of the one or more alarm settings; determining if the physiological parameter value meets the selected adaptive alarm condition; and generating an alarm when the physiological parameter value meets the selected adaptive alarm condition.

In a third embodiment, a medical device is provided. The medical device includes a signal input configured to acquire a physiological parameter value. The medical device also includes a memory storing one or more alarm settings associated with the physiological parameter value, wherein the one or more alarm settings comprise a physiological parameter value threshold and an integral value threshold. The medical device also includes a processor configured to determine if the physiological parameter value meets an alarm condition by integrating a difference between the physiological parameter value relative to the physiological parameter value threshold to generate an integral value and weighting the integral value. The medical device also includes an alarm generator configured to generate an alarm in response to a determination that the physiological parameter value meets the alarm condition, wherein the alarm condition is met when the weighted integral value is higher than the integral value threshold.

In a fourth embodiment, a method is provided that includes receiving a physiologic parameter, and a first alarm setting defining a first alarm condition adjusting a second alarm setting based on a sensitivity of the first alarm setting, the second alarm setting defining a second alarm condition; and triggering an alarm when the physiologic parameter meets the first alarm condition or the second alarm condition.

In a fifth embodiment, a method is provided that includes processing a photoplethysmograph (PPG) signal to calculate a physiologic parameter; comparing the physiologic parameter to a first alarm setting to identify a first alarm condition; comparing the physiologic parameter to a second alarm setting to identify a second alarm condition; and triggering an alarm when the first alarm condition or the second alarm condition is present, wherein the second alarm setting comprises a triggering condition that is a function of a sensitivity of the first alarm setting.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
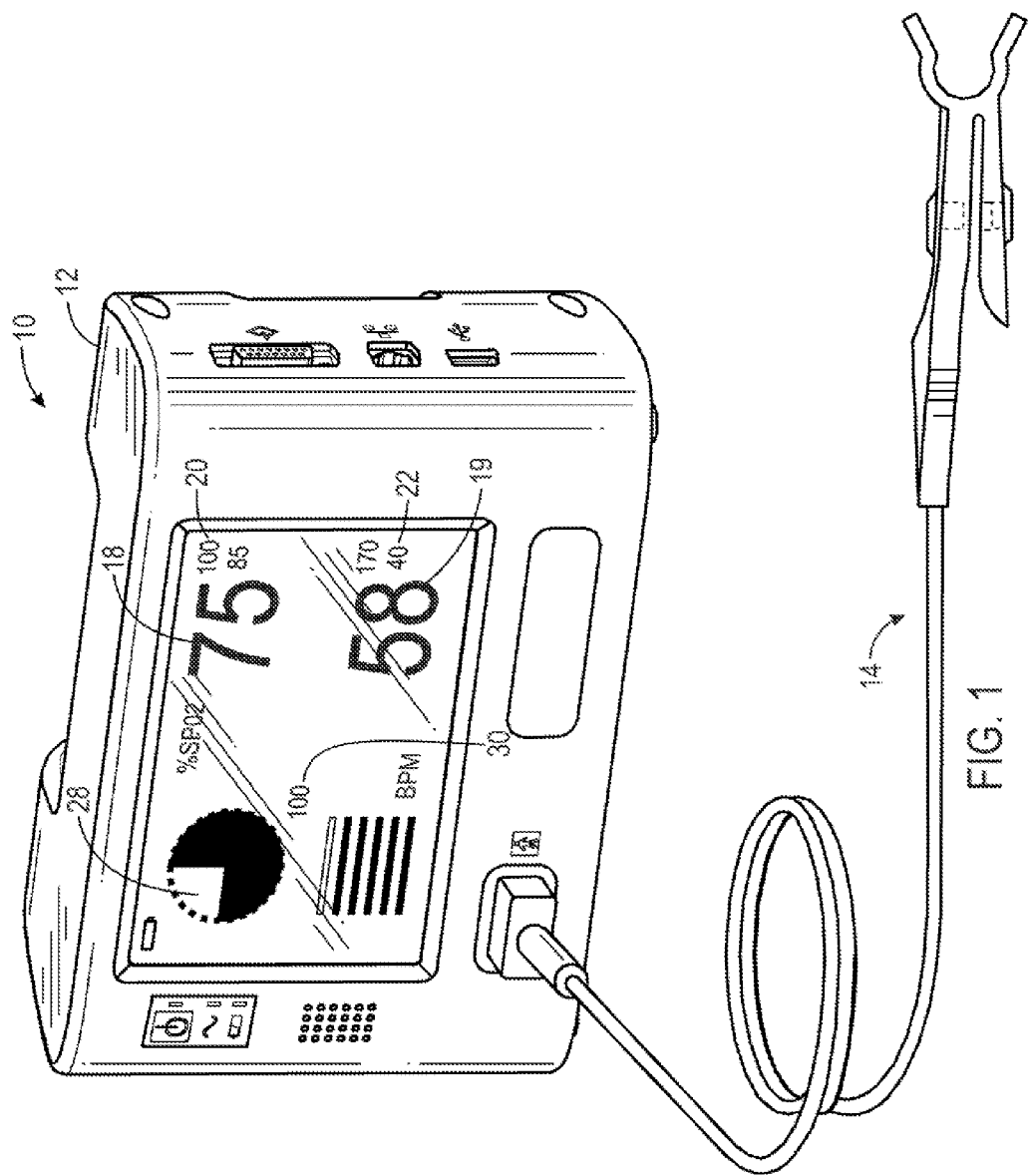
FIG. 1 is a perspective view of a medical monitor with an alarm indicator, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to adaptive alarm management in medical devices. In particular, medical monitors may include nuisance alarm reduction functionality to suppress alarms that are likely to be associated with motion artifacts or to be clinically insignificant. For example, a fast and short dip in a measured parameter that quickly returns to normal may be suppressed using a nuisance alarm reduction technique that does not trigger alarms for small changes in a parameter. In another example, both duration and size of an alarm condition may be considered by using an area under a curve or an integral of the measured parameter as a threshold for alarming. Such techniques may suppress alarms for measurements that vary only slightly from a threshold measured value, even over a longer period of time, so long as the measured value eventually returns to a value within a normal range during the alarm window. In yet another example, medical monitors may employ alarm event counters that do not trigger alarms until a threshold count of qualifying alarm events (e.g., threshold breaches) has occurred. Regardless of the type of nuisance alarm reduction technique employed, nuisance alarm reduction may result in suppression of certain alarm types that individually may be insignificant but that, in aggregate, may be of clinical interest. For example, frequent small desaturations (e.g., less than 3% change from a threshold) that may be masked by nuisance alarm reduction algorithms may be indicative of certain clinical conditions.

Accordingly, provided herein are adaptive alarm management techniques that provide increased alarm sensitivity or stringency while reducing nuisance alarms. In certain embodiments, the adaptive alarm management initiates automatic alarming if certain conditions are met (e.g., more than three threshold breaches per minute) that would not trigger an alarm under the conditions set forth by the monitor's standard alarm determination algorithm. In one embodiment, the adaptive alarm manager may be provided in parallel with or as an additional layer of alarms that occur along with or as part of a nuisance alarm reduction algorithm. For example, the adaptive alarm manager may alarm separately while a nuisance alarm reduction calculator continues to operate in the background. In such embodiments, the adaptive alarm manager may assess alarm conditions independently of the nuisance alarm reduction calculator. In another embodiment, the adaptive alarm manager may be implemented as part of a nuisance alarm reduction calculator to modify a nuisance alarm algorithm or other alarm calculation algorithm to weight certain alarm events more heavily or less heavily such that an alarm threshold is reached more quickly under certain conditions, e.g., by weighting certain physiological events (rapid desaturations, threshold breaches of a certain size) more heavily than others.

In one embodiment, the adaptive alarm manager may use the monitor alarm settings as a factor in determining whether to activate adaptive alarming and/or what type of adaptive alarming is appropriate. For example, the adaptive alarm manager may treat stringent alarm settings differently than less stringent alarm settings. For more stringent conditions, the adaptive alarm management techniques may provide minimal or no supplemental alarms to the default alarms determined under such stringent settings. In the case of more tolerant alarm settings, the adaptive alarm management techniques may provide more supplemental alarms, leading to increased alarming relative to the case without adaptive alarm management. Accordingly, the selectable alarm settings of a medical monitor maybe used to determine if and/or how much adaptive alarm management is implemented. By providing adaptive alarm management, medical monitor alarm settings and limits may be adjusted to very tolerant settings that nonetheless maintain alarming for events of clinical interest. As a result, the adaptive alarm management provides more granular control of alarm suppression that adapts as the alarm thresholds and limits are changed. In addition, the adaptive alarm management may be implemented along with existing alarm technologies so that clinicians may continue to interpret and acknowledge familiar alarm types.

With the foregoing in mind, FIG. 1 illustrates a medical monitoring system 10 that may be implemented with adaptive alarm management techniques in accordance with an embodiment. In the illustrated example, the system 10 includes a standalone medical monitor 12. While the illustrated medical monitor 12 is shown in the context of pulse oximetry monitoring, the present techniques for adaptive alarm management may also be used in conjunction with regional oximeters, electroencephalography (EEG) monitors, capnography monitors, depth of anesthesia monitors, and monitors that measure blood pressure, temperature, glucose, tissue water fraction, and/or other parameters. Further, the monitor 12 may be a multi-parameter monitor or may be part of a distributed monitoring system under control of a central station. The monitor 12 is coupled to a sensor 14 for monitoring one or more physiological parameters of a patient. For example, the monitor 12 may receive a physiological signal from the sensor 14, and the monitor 12 may be configured to generate a physiological waveform and/or calculate or measure one or more physiological parameters based on the physiological signal.

In the illustrated example, the monitor 12 is a pulse oximetry monitor and the sensor 14 is a pulse oximetry sensor. For example, the sensor 14 may include at least two emitters, which may emit light at two different wavelengths, and at least one detector for detecting photoplethysmography (PPG) signals from the patient tissue. The monitor 12 may include a processor configured to execute code (e.g., stored in a memory of the monitor 12 or received from another device) for filtering and processing the signals from the sensor 14 to calculate physiological parameters, such as oxygen saturation ($SpO_2$) and pulse rate. In other embodiments, the monitor 12 may calculate or measure a different parameter or combination of parameters. For example, the monitor 12 may be a regional oximeter. In such an embodiment, the sensor 14 includes at least two emitters and at least two detectors for detecting PPG signals at different depths, and the monitor 12 processes the PPG signals to calculate regional oxygen saturation ($rSO_2$). It should be appreciated that these are merely provided as examples, and other types of medical monitors may be used, such as the medical monitors noted above and multi-parameter monitors.

As illustrated in FIG. 1, the monitor 12 includes a display 16 displaying a one or more calculated physiological parameters, such as oxygen saturation 18, heart or pulse rate 19, or tissue perfusion, EEG, temperature, respiration rate, end tidal carbon dioxide ($etCO_2$), blood pressure, glucose, tissue water fraction, hemoglobin, or any other suitable physiological parameters. The display 16 may also display information related to alarms, such as oxygen saturation alarm thresholds 20 or heart rate alarm thresholds 22, monitor settings, and/or signal quality. In certain embodiments, the display 16 may be a touch screen display. The monitor 12 also includes various control inputs 21 for receiving user inputs. The control inputs 21 may be fixed function keys, programmable function keys, mechanical buttons, soft keys (corresponding to icons on the display 16), knobs, switches, or other mechanisms. In particular embodiments, the control inputs may be used by an operator to input or change alarm settings or limits that are used in conjunction with adaptive alarm management.

An alarm is generated by a medical device (such as the monitor 12 or a therapeutic device, such as a ventilator) when an alarm condition or protocol is met. Physiological alarm conditions trigger an alarm when a measured or calculated physiological parameter satisfies an alarm condition, such as when the parameter value crosses a threshold, deviates from a specified range, matches a stored pattern, deviates from a threshold for a specified time and/or extent (e.g., exceeding a limit on a value of an integral taken between the parameter value and a threshold), or meets other conditions that indicate a clinically significant event. Further, alarm conditions may be based on a combination of different alarm conditions, such as two physiological parameters each violating a respective limit, a combined alarm index violating a limit, or specified combinations of monitor and sensor status events. Referring to FIG. 1, when an alarm is generated by the monitor 12, textual or graphical alarm information may be displayed on the display 16, visible warning lights such as indicator lights 23 may be illuminated, and an audible warning may be sounded via speaker 24. The monitor 12 may include an alarm silence input 26 configured to silence active alarms, for example alarms that have been acknowledged by the caregiver. The alarm silence input 26 may silence the speaker portion of the alarm without affecting the calculation of alarm conditions or other alarm indicators.

In addition, certain monitors may include alarm graphics or icons. For example, an alarm counter graphic 28 may "count" or update according to a number or value based on the qualifying alarms. For example, in one embodiment, the alarm count may be a counter of the number of qualifying alarm events, whereby each breach of an alarm limit is a count. The alarm count may be associated with alarm count thresholds or settings that establish a number of alarm counts that may accumulate before an alarm is triggered. A higher setting allows more counts to accumulate than a lower setting and is less sensitive. In another embodiment, the alarm count may represent an integral count or a severity assessment. For example, in the illustrated embodiment, the alarm counter graphic 28 is a SatSeconds™ counter (provided by Covidien, LP, Boulder Colo.) that updates according to an integral value as discussed herein. The alarm counter graphic 28 may also include an associated alarm count threshold display 30 indicating to the user the user-selectable alarm counter limits in operation. In the illustrated embodiment, the alarm count threshold display 30 indicates an integral count of 100. Other settings for the alarm count threshold may be 10, 25, 50, etc. The alarm counter graphic 28 may be any suitable type, such a numeric display of a count value, a percentage of the counts that have occurred, or a graphical indicator that fills as the counts increase. In the illustrated embodiment, the integral counter is a circle that graphically fills as the integral count increases, with a full circle associated with an alarm trigger. As provided herein, adaptive alarm management may be implemented in conjunction with alarms related to a patient's physiological condition to refine alarm determination.

In one embodiment disclosed herein, adaptive alarm management may be used to augment integral count alarm determination. For example, an alarm manager may include a nuisance alarm suppressor that reduces the number of nuisance alarms in which a measured value such as $SpO_2$ is beyond an alarm threshold, but does not represent a clinically significant event. For example, if a caregiver feels that a desaturation of less than a few points below the lower alarm threshold for less than 5 seconds is not clinically meaningful, but rather constitutes a nuisance, the caregiver may set the integral alarm count threshold to "25" (5 points for 5 seconds). Then only a deeper desaturation or one of longer duration (i.e., a product that exceeds an integral count of 25) will initiate an alarm. In certain embodiments, the product of saturation-below-the-threshold and time are accumulated once per second, and this product is compared to the integral count threshold each time is it calculated. The effect of using the integral count alarm management method is to reduce the number of nuisance alarms and to alarm more specifically in response to events that are clinically meaningful as established previously by the caregiver via the alarm settings. An integral count-based alarm may modify conventional alarms, such as $SpO_2$ or pulse rate alarms that trigger alarms for measurement that fall below a specified fixed lower threshold or above a specified fixed upper threshold. While an integral count-based alarm is disclosed in conjunction with $SpO_2$ measurements, the techniques may be applied to pulse rate or other physiological measurements. Further, it should be understood that the adaptive alarm management techniques disclosed herein may be used in conjunction with other alarm techniques and with other types of medical monitoring.

Figure 2:
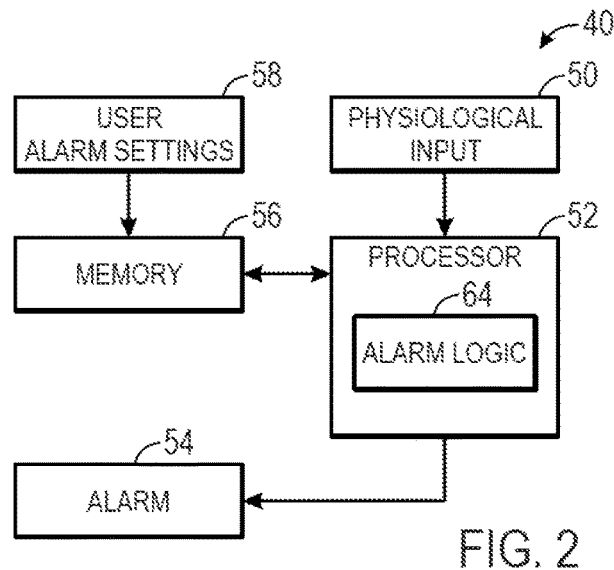
FIG. 2 is a block diagram of components of a medical system, in accordance with an embodiment.

A block diagram illustrating a processing system 40 that be implemented as an adaptive alarm manager is illustrated in FIG. 2. The processing system 40 may be incorporated into a monitor 12 (see FIG. 1) or within one or more components of the system 10 (see FIG. 1). The block diagram illustrates the interactions among some of the components of the system 40, including a physiological or signal input 50, processor 52, alarm 54, and memory 56 storing alarm settings 58. The processor 52 may receive physiologic data from the physiological input 50. The physiological input 50 may include an incoming raw or processed physiologic signal, or measured or calculated physiologic data. The physiological input 50 may be received from a sensor coupled to the patient (e.g., the sensor 14) or from other medical devices. The processor 52 may be configured to apply alarm logic 64 that generates an alarm based on the physiological input 50 and the stored alarm settings 58. In response to a generated alarm status, the processor 52 may activate the alarm 54 by activating a sound, a buzzer, a display, a vibration, a light, a text message, and/or any other suitable action. In operation, the processor 52 receives a physiological input 50, which may be in the form of a raw data (e.g., a photoplethysmographic waveform) or a pre-processed or processed signal that represents a physiological parameter value. The processor 52 may also execute other functions in monitoring, e.g., the processor 52 may be configured to execute instructions for processing the physiological input 50 to yield a physiological parameter value.

The system 40 may be implemented using one or more circuit components of the monitor 12 for calculating physiological parameters and generating alarms that may be implemented as hardware and/or software. It should be noted that the various components of the system 40 and/or the system 10 (see FIG. 1) may be connected via wired or wireless connections. The components may be separate from each other, or various combinations of components may be integrated together into a medical monitor or processor, or contained within a workstation with standard computer hardware (for example, processors, circuitry, logic circuits, memory, and the like). The system 10 may include processing devices such as microprocessors, microcontrollers, integrated circuits, control units, memory (such as read-only and/or random access memory), and/or other hardware. One or more system components may be housed within a smart cable, a cable adapter, or the like. Further, one or more system components may connect to an external device such as a medical sensor, a cellular or smart phone, tablet, other handheld device, laptop computer, monitor, or the like that may be configured to receive data and show the data on a display of the device.

The systems and methods described herein may be provided in the form of tangible and non-transitory machine-readable medium or media (such as a hard disk drive, etc.) having instructions recorded thereon for execution by a processor or computer. The set of instructions may include various commands that instruct the computer or processor to perform specific operations such as the methods and processes of the various embodiments described herein. The set of instructions may be in the form of a software program or application. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other suitable storage medium.

Figure 3:
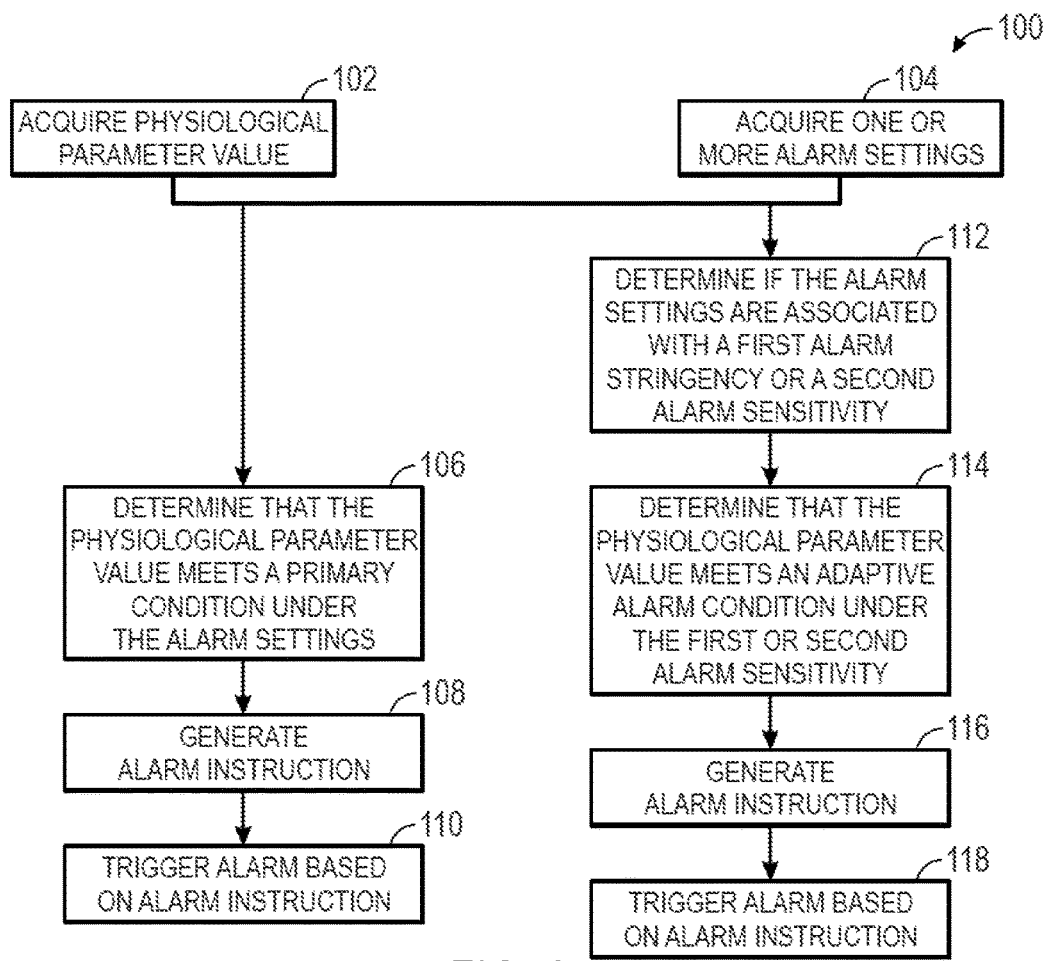
FIG. 3 illustrates a flow diagram of a method for implementing adaptive alarm management in parallel with other monitor alarms in accordance with an embodiment.

In certain embodiments of the disclosure, adaptive alarm management techniques may be implemented in parallel with other alarm determination calculators in the system 10. FIG. 3 is a flow diagram of method 100 of a parallel adaptive alarm determination technique. In the method 100, the adaptive alarm calculator and one or more other parallel alarms operate on the same acquired physiological data. Accordingly, the method acquires a physiological parameter value or values (block 102) and one or more alarm settings (block 104). While the flow diagram is discussed in conjunction with physiological parameter values, it should be understood that certain alarm techniques may alternatively or additionally use waveform data (e.g., for waveform pattern matching or waveform characteristic determination), parameter variability data, or other types of physiological data.

As provided herein, an adaptive alarm may adapt to certain alarm settings to trigger alarms in a manner dependent on the alarm settings in use. The one or more alarm settings acquired in the method 100 may include default alarms settings or user-selected alarm settings. For example, alarm settings may include upper or lower physiological parameter threshold values, physiological parameter threshold value ranges, time windows for collecting alarm data, alarm counter settings (e.g., alarm count thresholds, whereby exceeding or falling below a threshold triggers an alarm; alarm count threshold ranges), integral value thresholds or ranges, parameter variability thresholds or range, etc.

The acquired physiological parameter value or values may be used to determine if an alarm condition for the primary alarm is met (block 106) using an alarm calculator or algorithm. The primary alarm condition may be a conventional alarm condition, such as a parameter value threshold breach. In other embodiments, the alarm condition may be determined using a nuisance alarm reduction calculator or algorithm. In one embodiment, the nuisance alarm reduction algorithm may be a SatSeconds™ alarm as disclosed in U.S. Pat. No. 5,865,736, entitled, "METHOD AND APPARATUS FOR NUISANCE ALARM REDUCTIONS" or as in U.S. Pat. No. 8,401,606, entitled "NUISANCE ALARM REDUCTIONS IN A PHYSIOLOGICAL MONITOR," the disclosures of which are incorporated by reference in their entireties herein for all purposes.

In another embodiment, the primary alarm condition may be a saturation pattern detection (SPD) alarm calculator, such as those disclosed in U.S. Pat. No. 8,622,919, entitled "SYSTEM AND METHOD FOR FACILITATING OBSERVATION OF MONITORED PHYSIOLOGIC DATA," the disclosure of which is incorporated by reference in its entirety herein for all purposes. In the case of saturation pattern detection, the monitor may detect patterns in oxygen saturation that are indicative of ventilatory instability and provide alarms when such patterns are detected. In such embodiments, the selectable alarm settings may include configurable tolerance setting. For example, the user may have four choices for the sensitivity or tolerance setting: Off, Low, Medium, and High. When the sensitivity or tolerance setting is set to Off, an alarm based on detection of a saturation pattern may never be reported to the user. The other three tolerance settings (i.e., Low, Medium, and High) may each map to an SPD threshold value. For example, Low may map to an SPD threshold of 6, Medium may map to an SPD threshold of 15, and High may map to an SPD threshold of 24. In certain embodiments, adaptive alarm management may be used to augment SPD alarms, particularly for medium or high tolerance settings.

The primary alarm condition (block 106) may use the one or more alarm settings as variables in the alarm condition algorithm. In certain embodiments, a nuisance alarm reduction algorithm may use a plurality of alarm settings in determining if the alarm condition is met, including physiological parameter thresholds and/or alarm count thresholds. For example, if the primary alarm condition is a threshold breach, the one or more alarm settings may include a threshold value that is used as the comparator value in the alarm algorithm to determine in the alarm condition is met. If the alarm condition is met, the method 100 generates an alarm instruction (block 108) and triggers an alarm based on the alarm instruction (block 110). In addition to the primary alarm condition assessment (block 106), the method 100 also assesses adaptive alarms by determining if the one or more alarm settings are associated with a first or second alarm sensitivity (block 112). For example, if the one or more alarm settings include a selectable lower or upper parameter value threshold, the first sensitivity may be associated with a first value or range of values for the threshold while the second sensitivity is associated with a second value or range of values for the threshold. In one example, if the parameter is heart rate, a lower heart rate threshold of 40 may be associated with the first sensitivity while a lower heart rate threshold of 60 is associated with the second sensitivity. The associated alarm condition in the first parallel alarm (block 106) may be a heart rate bpm that drops below 40 in the first sensitivity or below 60 in the second sensitivity. In the example, the second sensitivity may be higher (i.e., associated with more sensitive alarming) while the first sensitivity is lower (i.e., associated with more tolerant or less sensitive alarms). The parallel alarm (block 106) augments more tolerant alarm settings to trigger alarms for clinical events that may otherwise be missed by providing a separate alarm with different alarm settings that are more sensitive than those of the primary alarm.

In one embodiment, while the primary alarm condition incorporates the alarm settings as variables in determining the alarm condition, the algorithm or technique used for assessing the primary alarm does not change depending on the alarm settings. That is, in one embodiment, the primary alarm condition algorithm does not adapt to the alarm settings by switching assessment algorithms, changing time windows, etc. In contrast, the adaptive alarm uses a sensitivity of the alarm settings to determine which adaptive alarm algorithm or calculator to employ. The adaptive alarm condition associated with the first alarm sensitivity is different than the adaptive alarm condition associated with the second alarm sensitivity. The adaptive alarm conditions for the first sensitivity or the second sensitivity may include the adaptive alarm conditions generally discussed herein. In one embodiment, the adaptive alarm condition for the first sensitivity triggers an alarm when the parameter value threshold, as established in the alarm settings, is breached more than three times in 10 seconds. The adaptive alarm condition for the second sensitivity triggers an alarm when the parameter value threshold, as established in the alarm settings, is breached more than three times in one minute. Accordingly, the adaptive alarm associated with the second sensitivity provides more sensitive alarm augmentation for volatile physiological parameter readings (e.g., for oxygen saturation values that include multiple small desaturations within one minute) that may otherwise be, at least in part, missed. That is, different adaptive alarms may provide different levels of alarm augmentation. The adaptive alarm runs together with the primary alarm, with each providing separate alarm instructions to trigger alarms. In this manner, the adaptive alarm augments the alarms generated by the primary alarm. The amount of augmentation depends on the alarm settings. For more tolerant alarm settings, the adaptive alarm may provide a greater degree of alarm augmentation and for less tolerant alarm settings, the adaptive alarm may provide no augmentation or limited augmentation. Further, the adaptive alarms do not reset or silence alarms generated by the primary alarm.

In cases where the one or more alarm settings are associated with a first sensitivity (which may be defined by the active alarm manager as being more or less stringent than the second sensitivity), the method 100 determines if the physiological parameter value meets an adaptive alarm condition associated with the first sensitivity (block 114). If the physiological parameter value meets the adaptive alarm condition, an alarm instruction is generated (block 116) and an alarm is triggered based on the alarm instruction (block 118). Similarly, if the one or more alarm settings are associated with a second sensitivity, the method 100 determines if the physiological parameter value meets an adaptive alarm condition associated with the second sensitivity to generate an alarm instruction.

Figure 4:
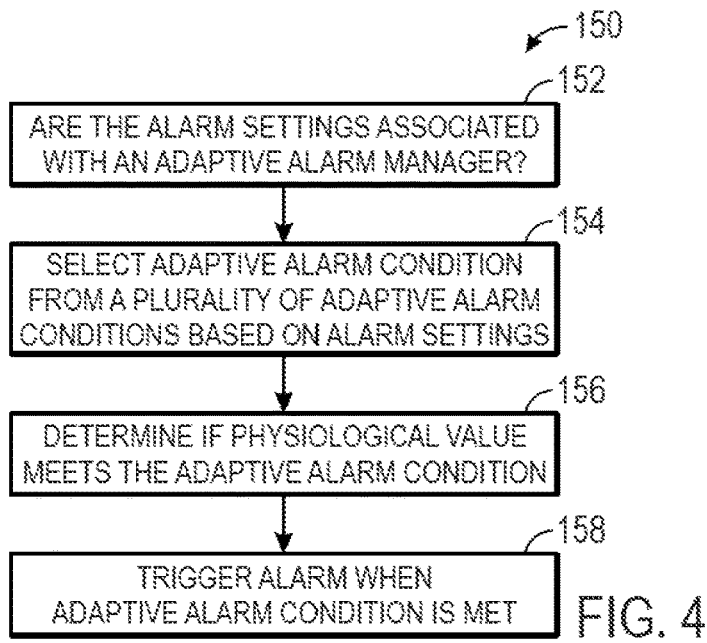
FIG. 4 illustrates a flow diagram of a method for implementing adaptive alarm management in accordance with an embodiment.

While the method 100 is disclosed in the context of two different adaptive alarm conditions (associated with the first sensitivity or the second sensitivity), the alarm settings may be associated with any number of stringencies and respective associated adaptive alarm conditions. FIG. 4 is a flow diagram of a method 150 that assesses whether the alarm settings are associated with an adaptive alarm manger (block 152). Certain alarm settings, for example extremely stringent or sensitive alarm settings, may be unlikely to benefit from augmentation. Accordingly, in certain embodiments of the present techniques, the adaptive alarm is not activated for particular primary alarm stringencies or sensitivities. In one example, if the primary alarm is set with a high threshold, the parallel alarm may not be activated. However, if the primary alarm limit is changed by the user to a lower threshold, the parallel alarm may be automatically activated to operate only in conjunction with the lower threshold and not the higher threshold. In another example, a low alarm count or integral count threshold is more sensitive than a relatively higher alarm count or integral count threshold. In certain embodiments, the parallel alarm is activated only for higher alarm count or integral count threshold settings and not lower alarm count or integral count threshold settings. In a specific embodiment, the adaptive alarm may be inactive for lower integral count alarm setting of 10 or 25 while the adaptive alarm is active for higher integral count settings. In yet another embodiment, the monitor 12 may be configured to indicate on the display when the adaptive alarm is active. For example, when the integral count settings are associated with the adaptive alarm, the alarm counter graphic 28 (see FIG. 1) may flash or change color.

For alarm settings that are associated with an adaptive alarm, the method 150 may assess the alarm settings to determine which adaptive alarm conditions apply (block 152). For example, a plurality of possible alarm settings may be associated with a respective plurality of different alarm conditions based on the assessed sensitivity of the alarm settings. For example, if the alarm settings include a parameter value threshold and a separate alarm count threshold, the two different settings may be combined, e.g., into a sensitivity index, to account for alarm settings with combinations of low sensitivity parameter value thresholds and high sensitivity alarm count thresholds. In one example, a integral count alarm includes an oxygen saturation threshold (e.g., 80%, 85%, 90%) as well as a SatSecond count (e.g., 10, 25, 50, 100). An alarm setting with a 90% oxygen saturation threshold and an integral count of 100 would have a mixed sensitivity while an alarm setting with a 90% oxygen saturation threshold and an integral count of 10 would have relatively high sensitivity. In another example, an upper bound of a parameter, such as heart rate, may be relatively stringent while the lower bound may be relatively tolerant. A sensitivity index or other technique for combining multiple alarm settings may be used to assess the sensitivity in such cases. In one example, the sensitivity index may be determined based on a spread between the upper and lower alarm limits. For example, for a heart rate alarm, if the lower alarm limit is 45 and the upper alarm limit is 135, the total spread between the limits is be 90. Alternatively, if the lower alarm limit is 45 but the upper alarm limit is 120, the total spread between the limits is 75. A lower overall spread may be associated with or mapped to a higher alarm sensitivity relative to a higher alarm spread. In other embodiments, a single alarm setting, such as a parameter value threshold or an alarm count threshold, may be controlling, even when used in conjunction with other alarm settings. In another example, a sensitivity index may be determined by assigning a score to each component of the alarm setting. A 90% oxygen saturation threshold (lower sensitivity) setting may be given a lower score than a 95% oxygen saturation threshold (relatively higher sensitivity) setting. Similarly, an integral count of 100 (lower sensitivity) may be given a lower score relative to an integral count of 10 (relatively higher sensitivity). The sensitivity index may reflect the combination score of various alarm settings in place.

While certain embodiments of the disclosure relate to associating primary alarm settings with first and second sensitivities, it should be understood that any number of alarm sensitivity levels are possible. The levels may be stepwise levels, whereby a range of alarm limits correspond to a first sensitivity and another range corresponds to a second sensitivity. For example, an integral count threshold range of 10-25 may represent a first sensitivity while an integral count threshold range of 25-50 may represent a second sensitivity and so on. In another embodiment, the sensitivities may be determined as a linear function, whereby an increase in a threshold setting of 1 unit correlates to a corresponding increase or decrease in a sensitivity level such that the sensitivity levels are relatively granular. In other embodiments, the adaptive alarm may be determined based on the alarm sensitivity index. The alarm sensitivity levels and their corresponding adaptive alarms may be stored in a memory of the system, such that selection of particular alarm settings automatically results in activation of the corresponding adaptive alarm. In one embodiment, the alarm sensitivity level or sensitivity index is used in a look-up table to select the associated adaptive alarm. In other embodiments, a user may provide input to select an adaptive alarm that is coupled to or activated under particular primary alarm settings.

Once the adaptive alarm condition is selected, the physiological parameter data may be evaluated under the selected adaptive alarm condition (block 156) to trigger an alarm when the condition is met (block 158). For example, the adaptive alarm may track desaturation events and trigger alarms once a certain count (e.g., 3) is reached in a fixed time period (e.g., 1 minute). The desaturation events may be defined differently for different alarm settings. In one embodiment used in conjunction with integral count alarms, for lower integral count settings of 10 or 25, the desaturation events may be counted as a 10% variation from the physiological parameter value threshold. For larger integral count settings of 100, the desaturation events may be counted as a 3% variation from the physiological parameter value threshold. Accordingly, if the user has selected an integral count of 25, a desaturation of 3% will not trigger the adaptive alarm. However, these desaturations will be tracked by the algorithm running in parallel to the adaptive alarm. In another embodiment, the count and/or the time window may vary for different alarm settings. For example, certain alarm settings, such as lower integral count settings, may be associated with adaptive alarms that count desaturation events over 10 seconds while other adaptive alarms associated count desaturation events over a minute.

Figure 5:
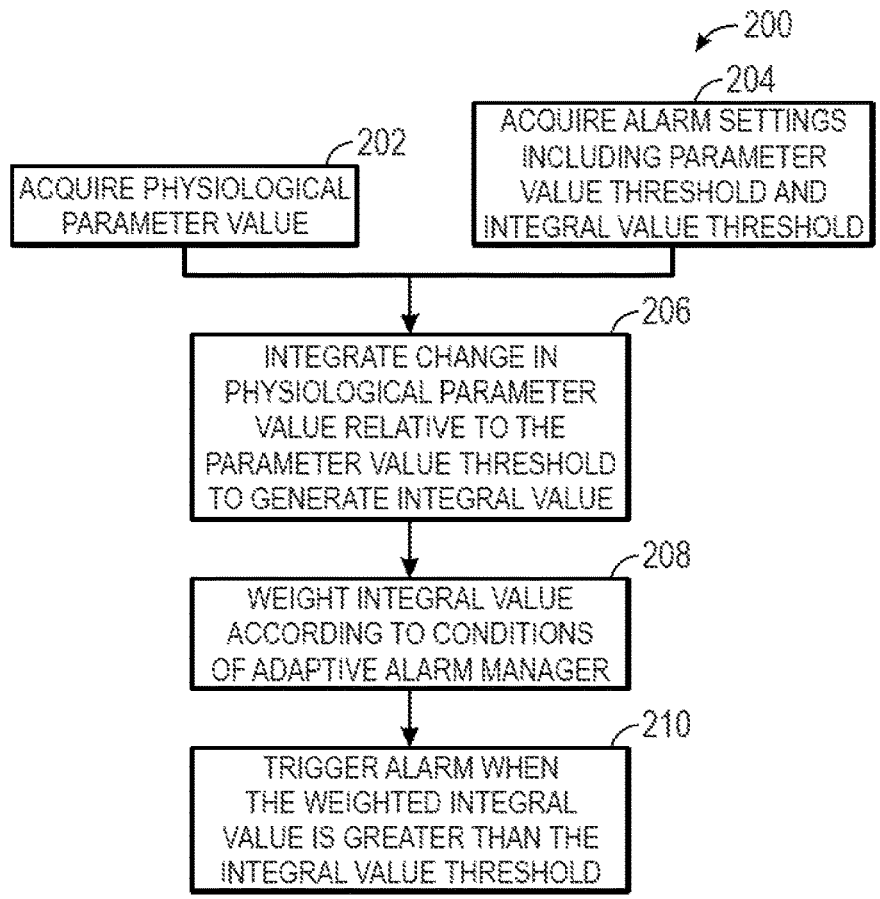
FIG. 5 illustrates a flow diagram of a method for implementing adaptive alarm management in conjunction with existing alarm determination techniques accordance with an embodiment.

In addition to operating in parallel to other monitor alarms, adaptive alarming techniques may be incorporated into existing alarm calculation algorithms. FIG. 5 is a method 200 using an adaptive alarm that is incorporated directly into a nuisance alarm calculator. The method 200 acquires a physiological parameter value or values (block 202) and one or more alarm settings that include a parameter threshold value and an integral value threshold (block 204). The method 200 assesses changes in the physiological parameter relative to the parameter value threshold to generate an integral value representative of the area under the curve for a particular time period (block 206). The integral value itself may then in turn trigger an alarm when the integral value threshold is exceeded. When implemented in conjunction with adaptive alarm management, the integral value may be weighted according to the alarm settings (block 208). For example, an unweighted integral value of 5 may be doubled to a weighted integral value of 10 if the alarm settings are stringent and several small desaturations occur in alarm time window. If the alarm settings are more tolerant, the integral value of 5 may be weighted to a lesser degree, for example halved to a weighted integral of 2.5, when such desaturations occur. Once the weighted integral value reached the integral value threshold, an alarm is triggered (210).

The method 200 may be used in conjunction with medical monitors configured for integral count-based alarming. The integral count may be determined by an integrator:

$$\text{integral count} = \sum_{i=1}^{ND} \Delta SpO2$$

where ND is the number of $SPO_2$ readings calculated every second during a desaturation event. In certain embodiments of the present techniques, the integrator may be nonlinear to reflect the severity of any desaturations. The integrator may include a weighting function w that is a function of $\Delta SpO_2$.

$$\text{integral count} = \sum_{i=1}^{ND} \Delta SpO2 \times w$$

The weight w may be set equal to unity until a large $\Delta SpO_2$ occurs whereby the weight may increase, for example w may become equal to two if $\Delta SpO2$ becomes greater than 10% relative to a threshold. In an embodiment, w may take multiple discrete values dependent upon $\Delta SpO_2$ value with respect to a threshold. Alternatively the value of w may map continuously to the value of $\Delta SpO_2$ with respect to a threshold. This mapping may be described by a function which may be linear, non-linear (e.g. logarithmic or exponential) or piecewise-defined. Alternatively the weight may increase based on a count of the number of threshold breaches. For example, weight, w, may increase to two if the count of threshold breaches during the previous minute is more than three.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that elements of the disclosed embodiments may be combined or exchanged with one another.

What is claimed is:

1. A method, comprising:
   acquiring a physiological parameter value and a first alarm setting defining a first alarm condition;
   identifying a sensitivity associated with the first alarm setting;
   selecting a second alarm setting based on the identified sensitivity associated with the first alarm setting, the second alarm setting defining a second alarm condition;
   determining in parallel whether the physiological parameter value meets the first alarm condition or the second alarm condition;
   generating a first alarm instruction upon a determination that the physiological parameter value meets the first alarm condition;
   generating a second alarm instruction upon a determination that the physiological parameter value meets the second alarm condition; and
   triggering an alarm in response to the generation of the first alarm instruction or the generation of the second alarm instruction.

2. The method of claim 1, wherein the sensitivity is a low alarm sensitivity associated with less frequent alarming under the first alarm condition or a high alarm sensitivity associated with more frequent alarming under the first alarm condition.

3. The method of claim 1, wherein identifying the sensitivity of the first alarm setting comprises identifying the sensitivity based on a stringency of the first alarm setting.

4. The method of claim 1, wherein the first alarm setting comprises a threshold value, and wherein identifying the sensitivity of the first alarm setting comprises identifying the sensitivity based on the threshold value associated with the first alarm setting.

5. The method of claim 1, wherein the first alarm setting comprises a first threshold value and an integral count value, and wherein the first threshold value and the integral count value are associated with a sensitivity score, and wherein identifying the sensitivity of the first alarm setting comprises identifying the sensitivity based on the sensitivity score.

6. The method of claim 5, wherein the integral count value is determined by integrating the physiological parameter value relative to a physiological parameter value threshold.

7. The method of claim 1, wherein one or more of the first alarm setting or the second alarm setting comprises one or both of a physiological parameter value threshold and an alarm count threshold.

8. The method of claim 7, wherein the first alarm setting comprises a first physiological parameter value threshold and a first alarm count threshold, associated with low alarm sensitivity, wherein the second alarm setting comprises a second physiological parameter value threshold and a second alarm count threshold, associated with high alarm sensitivity, and wherein the second physiological parameter value threshold is higher than the first physiological parameter value threshold and the second alarm count threshold is lower than the first alarm count threshold.

9. The method of claim 1, wherein the physiological parameter value comprises a set of physiological parameter values.

10. The method of claim 1, wherein the second alarm condition comprises a first number of breaches of a physiological parameter value threshold over a time period, wherein the physiological parameter value threshold is determined by the second alarm setting.

11. The method of claim 1, comprising acquiring a third alarm setting and identifying a sensitivity of the third alarm setting; and generating a third alarm instruction upon a determination that the physiological parameter meets a third alarm condition wherein the third alarm condition is selected based on the sensitivity of the third alarm setting.

12. The method of claim 11, wherein the second alarm condition comprises a pre-determined number of breaches of a first physiological parameter value threshold over a first time period and the third alarm condition comprises the pre-determined number of breaches of a second physiological parameter value threshold over a second time period, wherein the first time period is longer than the second time period, the first physiological parameter value threshold is associated with a first alarm sensitivity, and the second physiological parameter value threshold is associated with a second alarm sensitivity.

13. The method of claim 11, wherein the second alarm condition comprises a first number of breaches of a first physiological parameter value threshold over a time period and the third alarm condition comprises a second number of breaches of a second physiological parameter value threshold over the time period, wherein the first physiological parameter value threshold is associated with a first alarm sensitivity and the second physiological parameter value threshold is associated with a second alarm sensitivity.

14. The method of claim 1, wherein the physiological parameter value comprises an oxygen saturation value.

15. The method of claim 1, comprising receiving user input related to the first alarm setting.

16. A method, comprising:
   receiving a physiologic parameter, and a first alarm setting defining a first alarm condition;
   determining that the first alarm setting is associated with a first alarm sensitivity;
   identifying a second alarm setting defining a second alarm condition, the second alarm setting being associated with a second alarm sensitivity that is lower than the first alarm sensitivity;
   adjusting the second alarm setting such that the second alarm sensitivity becomes higher than the first alarm sensitivity;
   determining in parallel whether the physiologic parameter meets the first alarm condition or the second alarm condition;
   generating a second alarm instruction upon a determination that the physiologic parameter meets the second alarm condition but not the first alarm condition; and
   triggering an alarm in response to the second alarm instruction.

17. A method, comprising:
   processing a photoplethysmograph (PPG) signal to calculate a physiologic parameter;
   comparing the physiologic parameter to a first alarm setting to identify a first alarm condition, wherein the first alarm setting is associated with a first alarm sensitivity;
   comparing the physiologic parameter to a second alarm setting to identify a second alarm condition, wherein a second alarm sensitivity associated with the second alarm setting is based on the first alarm sensitivity, and wherein the second alarm sensitivity is higher than the first alarm sensitivity;

determining in parallel the physiologic parameter meets the second alarm condition but not the first alarm condition; and triggering an alarm associated with the second alarm setting in response to determining the physiologic parameter meets the second alarm condition but not the first alarm condition.

* * * * *